US006790964B1

United States Patent
Terashima et al.

(10) Patent No.: US 6,790,964 B1
(45) Date of Patent: Sep. 14, 2004

(54) PROCESS FOR THE PREPARATION OF 7-AZABICYCLO[4.1.0]HEPT-3-ENE-3-CARBOXYLIC ACID ESTERS

(75) Inventors: Shiro Terashima, Tokyo (JP); Katsuji Ujita, Okayama (JP); Akihiro Ishiwata, Tokyo (JP)

(73) Assignees: Sagami Chemical Research Center, Ayase (JP); Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 10/111,910

(22) PCT Filed: Oct. 27, 2000

(86) PCT No.: PCT/JP00/07578

§ 371 (c)(1),
(2), (4) Date: Aug. 13, 2002

(87) PCT Pub. No.: WO01/32617

PCT Pub. Date: May 10, 2001

(30) Foreign Application Priority Data

Nov. 2, 1999 (JP) .......................................... 11-312616

(51) Int. Cl.[7] .......................... C07D 203/26; C07C 47/52
(52) U.S. Cl. .......................... 548/961; 568/435; 568/436
(58) Field of Search ........................................ 548/961

(56) References Cited

U.S. PATENT DOCUMENTS

| | | | |
|---|---|---|---|
| 5,763,483 A | 6/1998 | Bischofberger et al. | |
| 5,834,618 A | 11/1998 | Terashima et al. | 558/408 |
| 5,866,601 A | 2/1999 | Lew et al. | 514/459 |
| 6,437,171 B1 * | 8/2002 | Karpf et al. | 560/125 |

FOREIGN PATENT DOCUMENTS

| | | |
|---|---|---|
| WO | 96/26933 | 9/1996 |
| WO | 98/07685 | 2/1998 |
| WO | 99/14185 | 3/1999 |

OTHER PUBLICATIONS

John C. Rohloff et al.: "Practical total synthesis of the anti–influenza drug GS–4104" J. Org. Chem., vol. 63, pp. 4545–4550 1998.
C.U. Kim et al.: "Influenza neuraminidase inhibitors prossessing a novel hydrophobic interaction in the enzyme active site: Design, synthesis, and structural analysis of carbocyclic slalic acid analogues with potent anti–influenzaactivity" J. Am. Chem. Soc., vol. 119, No. 4, pp. 681–690 1997.

* cited by examiner

Primary Examiner—Cecilia Tsang
Assistant Examiner—Ebenezer Sackey
(74) Attorney, Agent, or Firm—Oblon, Spivak, McClelland, Maier & Neustadt, P.C.

(57) ABSTRACT

The present invention provides a method of producing 7-azabicyclo[4.1.0]hept-3-ene-3-carboxylic acid ester (VII) economically, industrially advantageously and efficiently in a large amount. The present invention relates to a production method of compound (VII), which includes reacting epoxide (I) with amine (II) to give aminodiol (III), reacting the aminodiol (III) with a sulfonylating agent in the presence of a base to give azabicyclohept-2-ene (IV), reacting the azabicyclohept-2-ene (IV) with alcohol (V) in the presence of a Lewis acid to give azabicyclohept-3-ene (VI), and eliminating the 7-position substituent $R^2$ from the azabicyclohept-3-ene (VI)

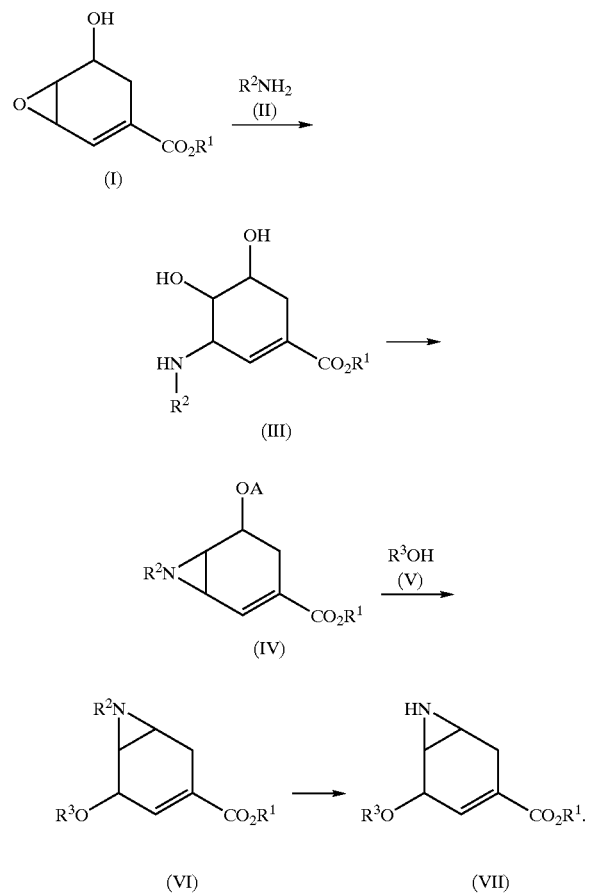

8 Claims, No Drawings

PROCESS FOR THE PREPARATION OF 7-AZABICYCLO[4.1.0]HEPT-3-ENE-3-CARBOXYLIC ACID ESTERS

TECHNICAL FIELD

The present invention relates to a production method of 7-azabicyclo[4.1.0]hept-3-ene-3-carboxylic acid ester. 7-Azabicyclo[4.1.0]hept-3-ene-3-carboxylic acid ester, such as ethyl (1α,5α,6α)-5-(1-ethylpropoxy)-7-azabicyclo[4.1.0]hept-3-ene-3-carboxylate, obtained by the present invention, is useful as a synthetic intermediate for GS4104 represented by the following formula. GS4104 is a compound under development as a novel agent for the prophylaxis and treatment of influenza based on the action to prevent viral growth by inhibiting neuraminidase present on the surface of influenza virus (hereinafter to be generally referred to as anti-influenza drug) [see Journal of Organic Chemistry (J. Org. Chem.), vol. 63, p. 4545 (1998); Journal of American Chemical Society (J. Am. Chem. Soc.), vol. 119, p. 681 (1997)].

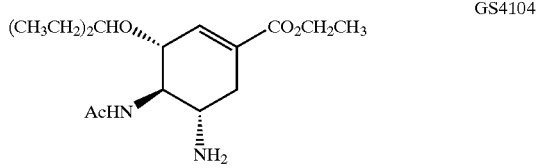

GS4104

BACKGROUND ART

As a conventional synthetic method of 7-azabicyclo[4.1.0]hept-3-ene-3-carboxylic acid ester, such as ethyl (1α,5α,6α)-5-(1-ethylpropoxy)-7-azabicyclo[4.1.0]hept-3-ene-3-carboxylate, a synthetic method wherein shikimic acid is used as a starting material [see Journal of Organic Chemistry (J. Org. Chem.), vol. 63, p. 4545 (1998); WO 99/14185; WO 98/07685], and a synthetic method wherein guinic acid is used as a starting material [see Journal of American Chemical Society (J. Am. Chem. Soc.), vol. 119, p. 681 (1997)] and the like are known.

The shikimic acid and quinic acid used as a starting material for the conventional synthetic method of ethyl (1α,5α,6α)-5-(1-ethylpropoxy)-7-azabicyclo[4.1.0]hept-3-ene-3-carboxylate are produced in less amounts and expensive. All the above-mentioned methods require many reaction steps. As widely known, influenza often becomes an epidemic disease worldwide, and an anti-influenza drug is required to be economical and supplied in a large amount. The above-mentioned production methods are not necessarily advantageous as a production method of the intermediate for GS4104 under development as an anti-influenza drug from the industrial viewpoint, and there is a demand for a synthetic method capable of economical production in a large amount.

DISCLOSURE OF INVENTION

It is therefore an object of the present invention to provide a production method of a 7-azabicyclo[4.1.0]hept-3-ene-3-carboxylic acid ester, such as ethyl (1α,5α,6α)-5-(1-ethylpropoxy)-7-azabicyclo[4.1.0]hept-3-ene-3-carboxylate, useful as a synthetic intermediate for GS4104 under development as an anti-influenza drug, economically, industrially advantageously and efficiently in a large amount.

According to the present invention, the above-mentioned objects can be achieved by providing
1) a production method of a 7-azabicyclo[4.1.0]hept-3-ene-3-carboxylic acid ester of the formula (VII)

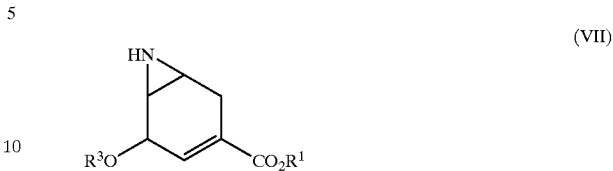

(VII)

wherein $R^1$ is an alkyl group optionally having substituents, a cycloalkyl group optionally having substituents, an aryl group optionally having substituents or an aralkyl group optionally having substituents and $R^3$ is an alkyl group optionally having substituents, a cycloalkyl group optionally having substituents, an alkenyl group optionally having substituents, an aryl group optionally having substituents or an aralkyl group optionally having substituents [hereinafter to be abbreviated as 7-azabicyclo[4.1.0]hept-3-ene-3-carboxylic acid ester (VII)], which comprises the steps of
(A) reacting a 5-hydroxy-7-oxabicyclo[4.1.0]hept-2-ene-3-carboxylic acid ester of the formula (I)

(I)

wherein $R^1$ is as defined above [hereinafter to be abbreviated as epoxide (I)] with an amine of the formula (II)

$$R^2NH_2 \qquad (II)$$

wherein $R^2$ is a hydrogen atom, an alkyl group optionally having substituents, a cycloalkyl group optionally having substituents, an alkenyl group optionally having substituents, an aryl group optionally having substituents or an aralkyl group optionally having substituents [hereinafter to be abbreviated as amine (II)] to give a 3-amino-4,5-dihydroxy-1-cyclohexene-1-carboxylic acid ester of the formula (III)

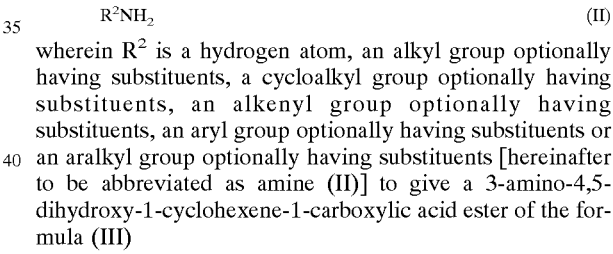

(III)

wherein $R^1$ and $R^2$ are as defined above [hereinafter to be abbreviated as aminodiol (III)],
(B) reacting the obtained aminodiol (III) with a sulfonylating agent in the presence of a base to give a 5-sulfonyloxy-7-azabicyclo[4.1.0]hept-2-ene-3-carboxylic acid ester of the formula (IV)

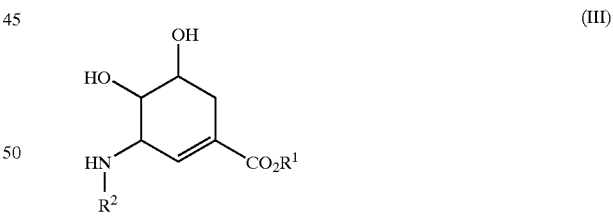

(IV)

wherein R¹ and R² are as defined above and A is an organic sulfonyl group [hereinafter to be abbreviated as azabicyclohept-2-ene (IV)], (C) reacting the obtained azabicyclohept-2-ene (IV) with an alcohol of the formula (V)

$$R^3OH \quad (V)$$

wherein R³ is as defined above [hereinafter to be abbreviated as alcohol (V)] in the presence of a Lewis acid to give a 5-oxy-7-azabicyclo[4.1.0]hept-3-ene-3-carboxylic acid ester of the formula (VI)

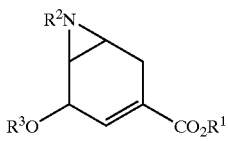

(VI)

wherein R¹, R² and R³ are as defined above [hereinafter to be abbreviated as azabicyclohept-3-ene (VI)], and (D) when R² is an alkyl group optionally having substituents, a cycloalkyl group optionally having substituents, an alkenyl group optionally having substituents, an aryl group optionally having substituents or an aralkyl group optionally having substituents, eliminating the 7-position substituent R² of the obtained azabicyclohept-3-ene (VI), (2) a production method of a 7-azabicyclo[4.1.0]hept-3-ene-3-carboxylic acid ester (VII), which comprises the steps of (A) reacting epoxide (I) with amine (II) to give aminodiol (III), (B) protecting an amino group of the obtained aminodiol (III) to give a 3-amino-4,5-dihydroxy-1-cyclohexene-1-carboxylic acid ester of the formula (VIII)

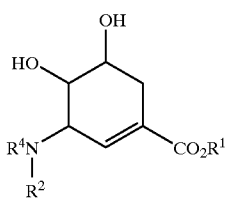

(VIII)

wherein R¹ and R² are as defined above and R⁴ is an amino-protecting group [hereinafter to be abbreviated as aminodiol (VIII)], (C) reacting the obtained aminodiol (VIII) with a sulfonylating agent in the presence of a base to give a 3-amino-4,5-disulfonyloxy-1-cyclohexene-1-carboxylic acid ester of the formula (IX)

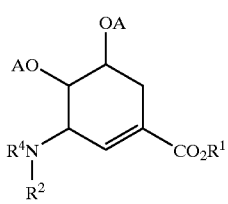

(IX)

wherein R¹, R² and R⁴ are as defined above and A is an organic sulfonyl group [hereinafter to be abbreviated as disulfonate (IX)], (D) removing the amino-protecting group from the obtained disulfonate (IX) to give a 3-amino-4,5-disulfonyloxy-1-cyclohexene-1-carboxylic acid ester of the formula (X)

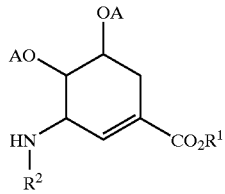

(X)

wherein R¹, R² and A are as defined above [hereinafter to be abbreviated as disulfonate (X)], (E) reacting the obtained disulfonate (X) with a base to give azabicyclohept-2-ene (IV), (F) reacting the obtained azabicyclohept-2-ene (IV) with alcohol (V) in the presence of a Lewis acid to give azabicyclohept-3-ene (VI), and (G) when R² is an alkyl group optionally having substituents, a cycloalkyl group optionally having substituents, an alkenyl group optionally having substituents, an aryl group optionally having substituents or an aralkyl group optionally having substituents, eliminating the 7-position substituent R² from the obtained azabicyclohept-3-ene (VI), (3) a production method of a 7-azabicyclo[4.1.0]hept-3-ene-3-carboxylic acid ester (VII), which comprises eliminating the 7-position substituent R²', from a 5-oxy-7-azabicyclo[4.1.0]hept-3-ene-3-carboxylic acid ester of the formula (VI')

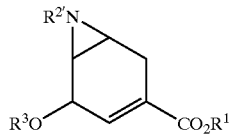

(VI')

wherein R²', is an alkyl group optionally having substituents, a cycloalkyl group optionally having substituents, an alkenyl group optionally having substituents, an aryl group optionally having substituents or an aralkyl group optionally having substituents, and R¹ and R³ are as defined above, (4) a production method of azabicyclohept-3-ene (VI), which comprises reacting azabicyclohept-2-ene (IV) with alcohol (V) in the presence of a Lewis acid, (5) a production method of azabicyclohept-2-ene (IV), which comprises reacting aminodiol (III) with a sulfonylating agent in the presence of a base, (6) a production method of azabicyclohept-2-ene (IV), which comprises reacting disulfonate (X) with a base, (7) a production method of azabicyclohept-2-ene (IV), which comprises (A) protecting an amino group of aminodiol (III) to give aminodiol (VIII), (B) reacting the obtained aminodiol (VIII) with a sulfonylating agent in the presence of a base to give disulfonate (IX), (C) removing the amino-protecting group of the obtained disulfonate (IX) to give disulfonate (X), and (D) reacting the obtained disulfonate (X) with a base, and (8) a production method of aminodiol (III), which comprises reacting epoxide (I) with amine (II).

In the above-mentioned formulas, the alkyl group represented by R¹, R² and R³ is a straight chain or branched chain alkyl group preferably having 1 to 10, more preferably 1 to 6 carbon atoms. Examples thereof include methyl group, ethyl group, propyl group, isopropyl group, n-butyl group, isobutyl group, tert-butyl group, pentyl group, 1-ethylpropyl group, hexyl group and the like. These alkyl groups may have substituents and examples of the substituent include alkoxyl group preferably having 1 to 10, more preferably 1 to 6 carbon atoms, such as methoxy group, ethoxy group, propoxy group, butoxy group and the like; halogen atom such as fluorine atom, chlorine atom, bromine atom and the like; cyano group; nitro group; and the like.

The cycloalkyl group represented by $R^1$, $R^2$ and $R^3$ is cycloalkyl group preferably having 3 to 8 carbon atoms and is exemplified by cyclopentyl group, cyclohexyl group, cyclooctyl group and the like. The aryl group represented by $R^1$, $R^2$ and $R^3$ is aryl group preferably having 6 to 10 carbon atoms, and is exemplified by phenyl group, naphthyl group and the like. The aralkyl group represented by $R^1$, $R^2$ and $R^3$ is aralkyl group wherein the alkyl moiety is alkyl group preferably having 1 to 6 carbon atoms and the aryl moiety has 1 to 3 aryl groups defined above. Examples thereof include benzyl group, diphenylmethyl group, triphenylmethyl group, phenethyl group and the like. These cycloalkyl group, aryl group and aralkyl group may have substituents and examples of the substituent include alkyl group preferably having 1 to 6 carbon atoms such as methyl group, ethyl group, propyl group, isopropyl group, n-butyl group, isobutyl group, tert-butyl group and the like; alkoxyl group preferably having 1 to 6 carbon atoms such as methoxy group, ethoxy group, propoxy group, butoxy group and the like; halogen atom such as fluorine atom, chlorine atom bromine atom and the like; cyano group; nitro group and the like.

The alkenyl group represented by $R^2$ and $R^3$ is a straight chain or branched chain alkenyl group preferably having 2 to 10, more preferably 2 to 6 carbon atoms. Examples thereof include allyl group, isopropenyl group, 2-methylallyl group and the like. These alkenyl groups may have substituents and examples of the substituent include alkoxyl group preferably having 1 to 6 carbon atoms such as methoxy group, ethoxy group, propoxy group, butoxy group and the like; halogen atom such as fluorine atom, chlorine atom, bromine atom and the like; cyano group; nitro group; and the like.

As $R^2$, an aralkyl group optionally having substituents (e.g., benzyl group, diphenylmethyl group) is preferable.

The protecting group of the amino group represented by $R^4$ is free of any particular limitation as long as it is generally used for protecting the amino group, and is exemplified by alkoxycarbonyl group such as tert-butoxycarbonyl group, 2,2,2-trichloroethoxycarbonyl group, 2-iodoethoxycarbonyl group, 2-trimethylsilylethoxycarbonyl group, 2-methylthioethoxycarbonyl group, 1,1-dimethylpropyloxycarbonyl group, 1-methyl-1-phenylethoxycarbonyl group, vinyloxycarbonyl group, allyloxycarbonyl group, cinnamyloxycarbonyl group, 1,1-dimethylpropynyloxycarbonyl group and the like; aralkyloxycarbonyl group such as 9-fluorenylmethoxycarbonyl group, benzyloxycarbonyl group, p-methoxybenzyloxycarbonyl group, 3,5-dimethoxybenzyloxycarbonyl group, p-nitrobenzyloxycarbonyl group, o-nitrobenzyloxycarbonyl group and the like; aralkyl group such as benzyl group, 2,4,6-trimethylbenzyl group, p-methoxybenzyl group, 3,5-dimethoxybenzyl group, p-nitrobenzyl group, o-nitrobenzyl group, o-chlorobenzyl group, p-chlorobenzyl group, o-bromobenzyl group, p-bromobenzyl group, 2,4-dichlorobenzyl group, p-cyanobenzyl group, m-chloro-p-acyloxybenzyl group, 9-anthrylmethyl group, diphenylmethyl group, phenyl(o-nitrophenyl)methyl group, di(2-pyridyl)methyl group, (4-pyridyl)methyl group, triphenylmethyl group and the like; acyl group such as formyl group, acetyl group, chloroacetyl group, dichloroacetyl group, trichloroacetyl group, trifluoroacetyl group, o-nitrophenylacetyl group, p-nitrophenylacetyl group, o-nitrophenoxyacetyl group, p-nitrophenoxyacetyl group, acetoacetyl group, pyridylacetyl group and the like; and the like.

The organic sulfonyl group represented by A is free of any particular limitation as long as it is bonded with an organic group, and is exemplified by alkylsulfonyl group optionally having substituents, arylsulfonyl group optionally having substituents, aralkylsulfonyl group optionally having substituents and the like. The alkyl moiety of the alkylsulfonyl group is alkyl group preferably having 1 to 6 carbon atoms. The aryl moiety of the arylsulfonyl group is, for example, phenyl group. The aryl moiety of the aralkylsulfonyl group is, for example, phenyl group, and the alkyl moiety is alkyl group preferably having 1 to 6 carbon atoms. The alkylsulfonyl group may have substituents, and examples of the substituent include alkoxyl group (alkoxyl group preferably having 1 to 6 carbon atoms), halogen atom, cyano group, nitro group and the like. The arylsulfonyl group and aralkylsulfonyl group may have substituents on the aromatic ring, and examples of the substituent include alkyl group (alkyl group preferably having 1 to 6 carbon atoms), alkoxyl group (alkoxyl group preferably having 1 to 6 carbon atoms), halogen atom, cyano group, nitro group and the like. The organic sulfonyl group represented by A is exemplified by methanesulfonyl group, ethanesulfonyl group, benzenesulfonyl group, toluenesulfonyl group, p-methoxybenzenesulfonyl group, 2,4,6-trimethylbenzenesulfonyl group, benzylsulfonyl group, p-methylbenzylsulfonyl group, trifluoromethanesulfonyl group and the like.

The production method of 7-azabicyclo[4.1.0]hept-3-ene-3-carboxylic acid ester (VII) of the present invention is shown in the following scheme, and includes two production methods of route (i) and route (ii), which can be determined as appropriate according to the kind of amine (II) to be used.

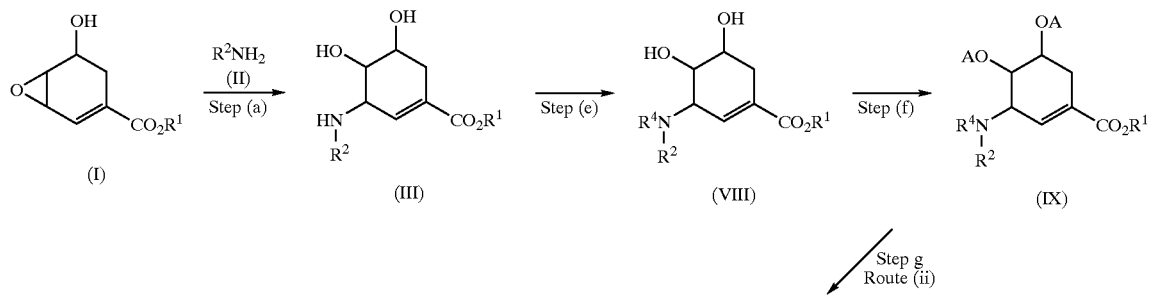

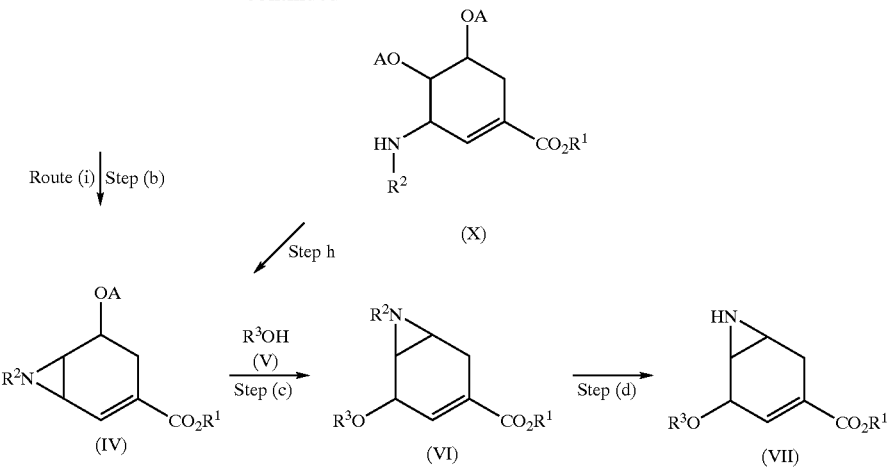

wherein $R^1$, $R^2$, $R^3$, $R^4$ and A are as defined above.

In the following, each step is explained.

(a): step for reacting epoxide (I) with amine (II) to give aminodiol (III)

Examples of the amine (II) include ammonia, methylamine, ethylamine, propylamine, n-butylamine, cyclohexylamine, cyclooctylamine, allylamine, isopropenylamine, aniline, 4-methylphenylamine, benzylamine, benzhydrylamine and the like. Of these, benzylamine and benzhydrylamine are particularly preferable. The amount of the amine (II) to be used is generally preferably 1 to 10-fold moles, particularly preferably 1 to 1.5-fold moles, per 1 mole of epoxide (I).

The reaction can be carried out in the presence or absence of a solvent. The solvent to be used is free of any particular limitation as long as it does not adversely affect the reaction. Examples thereof include aliphatic hydrocarbon such as hexane, heptane, octane and the like; aromatic hydrocarbon such as benzene, toluene, xylene, mesitylene and the like; ether such as diethyl ether, diisopropyl ether, tetrahydrofuran, dioxane and the like; and the like. When a solvent is used, the amount of the solvent to be used is free of any particular limitation, but it is generally preferably 1 to 10-fold weight, more preferably 1 to 3-fold weight, relative to epoxide (I).

The reaction temperature is preferably 20 to 200° C., more preferably 50° C. to 80° C. While the reaction time varies depending on the kind and the amount of epoxide (I), amine (II) and the solvent, it is generally within the range of 1 to 48 hours.

The reaction is carried out by, for example, mixing epoxide (I), amine (II) and a solvent as necessary and stirring the mixture at a given temperature.

The aminodiol (III) thus obtained can be purified and separated according to a method generally employed for the purification and separation of organic compounds. For example, the reaction mixture is concentrated, and the obtained concentrate is purified by distillation, column chromatography and the like.

(b): Step for reacting aminodiol (III) with a sulfonylating agent in the presence of a base to give azabicyclohept-2-ene (IV)

Examples of the base include tertiary amine such as trimethylamine, triethylamine, tripropylamine, tributylamine, trioctylamine, pyridine, collidine, lutidine and the like; alkaline metal hydride such as sodium hydride, potassium hydride and the like; alkaline metal carbonate such as sodium carbonate, potassium carbonate and the like; and the like. Of these, triethylamine, pyridine and lutidine are preferable. The amount of the base to be used is preferably 2 to 100-fold moles, more preferably 2 to 25-fold moles, per 1 mole of aminodiol (III).

Examples of the sulfonylating agent include organic sulfonyl halide such as methanesulfonyl chloride, methanesulfonyl fluoride, ethanesulfonyl chloride, ethanesulfonyl bromide, benzenesulfonyl chloride, benzenesulfonyl bromide, benzenesulfonyl fluoride, toluenesulfonyl chloride, toluenesulfonyl bromide, toluenesulfonyl fluoride, p-methoxybenzenesulfonyl chloride, 2,4,6-trimethylbenzenesulfonyl chloride, benzylsulfonyl chloride, p-methylbenzylsulfonyl chloride, trifluoromethanesulfonyl chloride and-the like; sulfonic anhydride such as methanesulfonic anhydride, p-toluenesulfonic anhydride, trifluoromethanesulfonic anhydride and the like; and the like. The amount of the sulfonylating agent to be used is preferably 2 to 10-fold moles, more preferably 2 to 5-fold moles, per 1 mole of aminodiol (III).

The reaction is preferably carried out in a solvent. The solvent to be used is free of any particular limitation as long as it does not adversely affect the reaction. Examples thereof include aliphatic hydrocarbon such as hexane, heptane, octane and the like; aromatic hydrocarbon such as benzene, toluene, xylene, mesitylene and the like; ether such as diethyl ether, diisopropyl ether, tetrahydrofuran, dioxane and the like; halogenated hydrocarbon such as dichloromethane, chloroform, carbon tetrachloride, 1,2-dichloroethane and the like; and the like. The amount of the solvent to be used is free of any particular limitation, but it is generally preferably 1 to 100-fold weight, more preferably 1 to 10-fold weight, relative to aminodiol (III).

The reaction temperature is preferably −20° C. to 1500° C., more preferably 10° C. to 80° C. While the reaction time varies depending on the kind and the amount of aminodiol (III), base, sulfonylating agent and solvent, it is generally within the range of 1 to 48 hours.

The reaction is carried out by, for example, dissolving aminodiol (III) and a base in a solvent, adding a sulfonylating agent and stirring the mixture at a given temperature.

The azabicyclohept-2-ene (IV) thus obtained can be purified and separated according to a method generally employed for the purification and separation of organic compounds. For example, the reaction mixture is poured into water, extracted with aliphatic hydrocarbon such as n-hexane and the like, aromatic hydrocarbon such as toluene and the like, halogenated hydrocarbon such as dichloromethane and the like, ether such as diethyl ether, diisopropyl ether and the like; and the like, and the extract is concentrated and the obtained concentrate is purified by distillation, column chromatography and the like.

(c): step for reacting azabicyclohept-2-ene (IV) and alcohol (V) in the presence of Lewis acid to-give azabicyclohept-3-ene (VI)

Examples of the alcohol (V) include primary alcohol such as methanol, ethanol, 1-propanol, 1-octanol, allyl alcohol, benzyl alcohol and the like; secondary alcohol such as isopropanol, 2-butanol, 3-pentanol, cyclopentanol, cyclohexanol and the like. Of these, the use of 3-pentanol as alcohol (V) is particularly preferable from the viewpoint of synthesis of ethyl (1α,5α,6α)-5-(1-ethylpropoxy)-7-azabicyclo[4.1.0]hept-3-ene-3-carboxylate, which is a synthetic intermediate for GS4104. The amount of the alcohol (V) to be used is preferably 1 to 200-fold moles, more preferably 10 to 100-fold moles, per 1 mole of azabicyclohept-2-ene (IV).

Examples of the Lewis acid include boron trifluoride-etherate, aluminum chloride, zinc chloride, zinc iodide, titanium tetrachloride and the like. The amount of the Lewis acid to be used is preferably 0.1 to 30-fold moles, more preferably 1 to 10-fold moles, per 1 mole of azabicyclohept-2-ene (IV).

The reaction can be carried out in the presence or absence of a solvent. Examples of the solvent to be used is free of any particular limitation as long as it does not adversely affect the reaction. Examples of the solvent include aliphatic hydrocarbon such as hexane, heptane, octane and the like; aromatic hydrocarbon such as benzene, toluene, xylene, mesitylene and the like; ether such as diethyl ether, diisopropyl ether, tetrahydrofuran, dioxane and the like; halogenated hydrocarbon such as dichloromethane, chloroform, carbon tetrachloride, -1,2-dichloroethane and the like; and the like. When a solvent is used, the amount thereof is free of any particular limitation. It is generally preferably 1 to 100-fold weight, more preferably 1 to 10-fold weight relative to azabicyclohept-2-ene (IV).

For efficient progress of the reaction, a base may be also present during the reaction. Examples of the base include amine such as triethylamine, pyridine, collidine, lutidine and the like; alkaline metal hydride such as sodium hydride, potassium hydride and the like; alkaline metal carbonate such as sodium carbonate, potassium carbonate and the like; and the like. When a base is co-used, the amount thereof is free of any particular limitation, but it is preferably 2 to 100-fold moles, more preferably 2 to 25-fold moles, relative to azabicyclohept-2-ene (IV). 10 The reaction temperature is preferably 0–100° C., more preferably 10–80° C. While the reaction time varies depending on the kind and the amount of azabicyclohept-2-ene (IV), alcohol (V), Lewis acid and solvent, it is generally 0.5 to 10 hours.

The reaction is carried out by, for example, mixing azabicyclohept-2-ene (IV), alcohol (V), Lewis acid and a solvent as necessary and stirring the mixture at a given temperature. When a base is further co-used for the reaction, the base is preferably added after start of stirring as mentioned above. In this case, the given amount of the base may be added at once or added by several-divided portions.

The azabicyclohept-3-ene (VI) thus obtained can be purified and separated according to a method generally employed for the purification and separation of organic compounds. For example, the reaction mixture is poured into water, extracted with aliphatic hydrocarbon such as n-hexane and the like, aromatic hydrocarbon such as toluene and the like, ether such as diethyl ether, diisopropyl ether and the like; and the like, and the extract is concentrated and the obtained concentrate is purified by distillation, column chromatography and the like.

When $R^2$ is a hydrogen atom, the objective 7-azabicyclo[4.1.0]hept-3-ene-3-carboxylic acid ester (VII) can be obtained at this stage without performing the next step (d).

(d): step for obtaining 7-azabicyclo[4.1.0]hept-3-ene-3-carboxylic acid ester (VII) by eliminating the 7-position substituent $R^2$ from azabicyclohept-2-ene (VI) The 7-position substituent $R^2$ can be eliminated from azabicyclohept-3-ene (VI) by, for example, a treatment with an acid or according to a known method using catalytic hydrogenation (T. W. Green, "Protective Groups in organic Synthesis," John-Wiley & Sons, New York, pp 218–287 (1981)).

For the treatment with an acid, azabicyclohept-3-ene (VI) is brought into contact with, for example, a solution of hydrogen chloride or hydrogen bromide in alcohol such as ethanol and the like. Examples of the catalytic hydrogenation include a method including reacting azabicyclohept-3-ene (VI) with a hydrogen source such as hydrogen, formic acid and the like in the presence of a catalyst such as Raney-nickel, palladium-carbon and the like.

Particularly, when the 7-position substituent $R^2$ is an aralkyl group, such as benzyl group and diphenylmethyl group, a method for eliminating the 7-position substituent using palladium-carbon as a catalyst and formic acid as a hydrogen source is particularly preferable, because only the 7-position substituent can be selectively eliminated without reducing the double bond of cyclohexene ring. The palladium-carbon to be used here may be those commercially available for hydrogenation, where no limitation is imposed on the amount of palladium to be carried and the like. The weight of palladium-carbon to be used is preferably 0.1 to 10-fold weight, more preferably 0.5 to 3-fold weight, relative to azabicyclohept-3-ene (VI). The amount of the formic acid to be used is preferably 1 to 100-fold moles, more preferably 1 to 10-fold moles, relative to azabicyclohept-3-ene (VI). The reaction is preferably carried out in a solvent. As the solvent, alcohol such as methanol, ethanol and the like; aliphatic hydrocarbon such as hexane, heptane, octane and the like; ether such as diethyl ether, diisopropyl ether, tetrahydrofuran, dioxane and the like; aromatic hydrocarbon such as benzene, toluene, xylene, mesitylene and the like; halogenated hydrocarbon such as dichloromethane, chloroform, carbon tetrachloride, 1,2-dichloroethane and the like; and the like are exemplified. Of these, aliphatic hydrocarbon such as hexane, heptane, octane and the like; alcohol such as methanol, ethanol and the like are more preferable. The amount of the solvent to be used is free of any particular limitation but it is generally preferably 1 to 100-fold weight, more preferably 1 to 10-fold weight, relative to azabicyclohept-3-ene (VI). The reaction temperature is preferably −50 to 100° C., more preferably −20 to 50° C.

The 7-azabicyclo[4.1.0]hept-3-ene-3-carboxylic acid ester (VII) thus obtained can be purified and separated according to a method generally employed for the purification and separation of organic compounds. For example, the reaction mixture is neutralized or filtrated, then concentrated, and the obtained concentrate is purified by distillation, column chromatography and the like.

(e): step to protect amino group of aminodiol (III) to give aminodiol (VIII)

As the protecting group used to protect amino group of aminodiol (III), the protecting groups generally used for the protection of amino group can be used. Of these protecting groups, those stable under the reaction conditions, under which to produce disulfonate (IX) in the next step (f), and capable of being removed when the protecting group is to be quickly removed in step (g) to be mentioned below, without impairing other moieties of disulfonate (X) are particularly preferable. Examples of the amino-protecting group include alkoxycarbonyl group such as tert-butoxycarbonyl group, 2,2,2-trichloroethoxycarbonyl group, 1,1-dimethylpropyloxycarbonyl group and the like; aralkyloxycarbonyl group such as p-methoxybenzyloxycarbonyl group and the like. Of these, tert-butoxycarbonyl group is particularly preferable. These amino-protecting groups can be introduced by a known method (T. W. Green, "Protective Groups in Organic Synthesis," John-Wiley & Sons, New York, pp 218–287 (1981)). For example, tert-butoxycarbonyl group can be introduced by the use of di-tert-butyl dicarbonate in an amount of 1 to 3-fold moles, more preferably 1 to 1.2-fold moles, relative to-aminodiol (III).

The reaction to protect amino group is preferably carried out in the presence of a solvent. The solvent to be used is free of any particular limitation as long as it does not adversely affect the reaction and examples thereof include halogenated hydrocarbon such as dichloromethane, chloroform, carbon tetrachloride, 1,2-dichloroethane and the like; aliphatic hydrocarbon such as hexane, heptane, octane and the like; aromatic hydrocarbon such as benzene, toluene, xylene, mesitylene and the like; ether such as diethyl ether, diisopropyl ether, tetrahydrofuran, dioxane and the like; acetonitrile; and the like. The amount of the solvent to be used is free of any particular limitation, but generally it is preferably 1 to 100-fold weight, more preferably 1 to 10-fold weight, relative to aminodiol (III).

The reaction temperature is preferably −20 to 150° C., more preferably 20 to 80° C.

The aminodiol (VIII) thus obtained can be purified and separated according to a method generally employed for the purification and separation of organic compounds. For example, the reaction mixture is poured into water, extracted with aliphatic hydrocarbon such as n-hexane and the like, aromatic hydrocarbon such as toluene and the like, ether such as diethyl ether, diisopropyl ether and the like; and the like, and the extract is concentrated and the obtained concentrate is purified by distillation, column chromatography and the like.

(f): step for reacting aminodiol (VIII) with a sulfonylating agent in the presence of a base to give disulfonate (IX)

As the sulfonylating agent, the compounds recited in the above-mentioned step (b) can be used. The amount of the sulfonylating agent to be used is preferably 2 to 10-fold moles, more preferably 2 to 5-fold moles, per 1 mole of aminodiol (VIII).

Examples of the base include tertiary amine such as trimethylamine, triethylamine, tripropylamine, tributylamine, trioctylamine, pyridine, collidine, lutidine and the like; alkaline metal hydride such as sodium hydride, potassium hydride and the like; alkaline metal carbonate such as sodium carbonate, potassium carbonate and the like; and the like. Of these, triethylamine, pyridine and lutidine are preferable. The amount of the base to be used is preferably 2 to 10-fold moles, more preferably 2 to 5-fold moles, per 1 mole of aminodiol (VIII).

The reaction is preferably carried out in the presence of a solvent. The solvent to be used is free of any particular limitation as long as it is not involved in the reaction. Examples thereof include aliphatic hydrocarbon such as hexane, heptane, octane and the like; aromatic hydrocarbon such as benzene, toluene, xylene, mesitylene and the like; ether such as diethyl ether, diisopropyl ether, tetrahydrofuran, dioxane and the like; halogenated hydrocarbon such as dichloromethane, chloroform, carbon tetrachloride, 1,2-dichloroethane and the like; and the like. The amount of the solvent to be used is free of any particular limitation but it is generally preferably 1 to 100-fold weight, more preferably 1 to 10-fold weight, relative to aminodiol (VIII).

The reaction temperature is preferably 0–50° C., more preferably 10–30° C. While the reaction time varies depending on the kind and the amount of aminodiol (VIII), base, sulfonylating agent and solvent, it is generally 1 to 48 hours.

The reaction is preferably carried out by, for example, dissolving aminodiol (VIII) and a base in a solvent, adjusting to a given temperature, adding a sulfonylating agent and stirring the mixture.

The disulfonate (IX) thus obtained can be purified and separated according to a method generally employed for the purification and separation of organic compounds. For example, the reaction mixture is poured into water, extracted with aliphatic hydrocarbon such as n-hexane and the like, aromatic hydrocarbon such as toluene and the like, ether such as diethyl ether, diisopropyl ether and the like; and the like, and the extract is concentrated and the obtained concentrate is purified by distillation, column chromatography and the like.

(g): step to remove amino-protecting group from disulfonate (IX) to give disulfonate (X)

The amino-protecting group can be removed from disulfonate (IX) according to a known method (T. W. Green, "Protective Groups in Organic Synthesis," John-Wiley & Sons, New York, pp 218–287 (1981)). When the amino-protecting group is tert-butoxycarbonyl group, it can be removed by using trifluoroacetic acid, trimethylbromosilane, trimethyliodosilane and the like and halogenated hydrocarbon such as dichloromethane, chloroform and the like as a solvent in a proportion of 1 to 100-fold weight, preferably 1 to 10-fold weight, relative to disulfonate (IX), at a reaction temperature of 0–50° C., preferably 10–30° C. The obtained disulfonate (X) can be purified and separated according to a method generally employed for the purification and separation of organic compounds. For example, the reaction mixture is poured into water, extracted with aliphatic hydrocarbon such as n-hexane and the like, aromatic hydrocarbon such as toluene and the like, ether such as diethyl ether, diisopropyl ether and the like; and the like, and the extract is concentrated and the obtained concentrate is purified by distillation, column chromatography and the like.

(h): step to react disulfonate (X) with a base to obtain azabicyclohept-2-ene (IV)

Examples of the base include tertiary amine such as trimethylamine, triethylamine, tripropylamine, tributylamine, trioctylamine, pyridine, collidine, lutidine and the like; alkaline metal hydride such as sodium hydride, potassium hydride and the like; alkaline metal carbonate such as sodium carbonate, potassium carbonate and the like; and the like. Of these, triethylamine, pyridine and lutidine are preferable. The amount of the base to be used is preferably 2 to 100-fold moles, more preferably 2 to 25-fold moles, per 1 mole of disulfonate (X).

The reaction is preferably carried out in the presence of a solvent. The solvent to be used is free of any particular limitation as long as it is not involved in the reaction. Examples thereof include aliphatic hydrocarbon such as hexane, heptane, octane and the like; aromatic hydrocarbon such as benzene; toluene, xylene, mesitylene and the like; ether such as diethyl ether, diisopropyl ether, tetrahydrofuran, dioxane and the like; halogenated hydrocarbon such as dichloromethane, chloroform, carbon tetrachloride, 1,2-dichloroethane and the like; and the like. The amount of the solvent to be used is free of any particular limitation, and generally it is preferably 1 to 100-fold weight, more preferably 1 to 10-fold weight, relative to disulfonate (X).

The reaction temperature is preferably 0–150° C., more preferably 20–80° C. While the reaction time varies depending on the kind and the amount of use of disulfonate (X), base and solvent, it is generally 1 to 48 hours.

The reaction is preferably carried out by, for example, dissolving disulfonate (X) and a base in a solvent and stirring the mixture at a given temperature.

The azabicyclohept-2-ene (IV) thus obtained can be purified and separated according to a method generally employed for the purification and separation of organic compounds. For example, the reaction mixture is poured into water, extracted with aliphatic hydrocarbon such as n-hexane and the like, aromatic hydrocarbon such as toluene and the like, ether such as diethyl ether, diisopropyl ether and the like; and the like, and the extract is concentrated and the obtained concentrate is purified by distillation, column chromatography and the like.

The epoxide (I), which is a starting material for the present invention, can be produced as shown in Reference Examples 1–3 to be mentioned below, wherein furan and acrylic acid ester of the formula (XI)

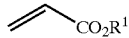

(XI)

wherein $R^1$ is as defined above, are subjected to a Diels-Alder reaction in the presence of Lewis acid, such as zinc iodide, zinc chloride, titanium tetrachloride and the like, the obtained compound is reacted with a base such as lithium diisopropylamide, lithium hexamethyldisilazide and the like to perform intramolecular retro-Michael reaction to give dieno alcohol of the formula (XII)

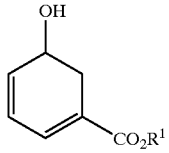

(XII)

wherein $R^1$ is as defined above [see Tetrahedron Letters, vol. 23, p. 5299 (1982)], and this dieno alcohol is reacted with peroxide such as magnesium monoperoxyphthalate, peracetic acid, m-chloroperbenzoic acid and the like [see Journal of American Chemical Society (J. Am. Chem. Soc.), vol. 104, p. 7036 (1982)].

According to the method described in Journal of Organic Chemistry (J. Org. Chem.), vol. 63, p. 4545 (1998), GS4104 can be synthesized from 7-azabicyclo[4.1.0]hept-3-ene-3-carboxylic acid ester (VII), such as ethyl (1α,5α,6α)-5-(1-ethylpropoxy)-7-azabicyclo[4.1.0]hept-3-ene-3-carboxylate obtained by the method of the present invention.

EXAMPLE

The present invention is described in more detail by means of the following Examples, which are not to be construed as limitative.

Reference Example 1

Synthesis of 2-ethoxycarbonyl-7-oxabicyclo[2.2.1]hept-5-ene

Furan (2.04 ml, 28 mmol), ethyl acrylate (2.06 ml, 20 mmol) and zinc iodide (1.92 g, 6 mmol) were placed in a sealed tube and the mixture was heated at 40° C. for 2 days. The reaction mixture was cooled to room temperature and diluted with ethyl acetate (100 ml). 10% Aqueous sodium thiosulfate solution (20 ml) was added, and the mixture was stirred at room temperature for 30 min. The organic layer was partitioned, washed with saturated brine (100 ml), and dried over anhydrous sodium sulfate. The components having a low boiling point, such as the solvent and the like, were distilled away. The obtained residue was purified by silica gel column chromatography (eluent: ethyl acetate/hexane= 1/10 (volume ratio)) to give 2-ethoxycarbonyl-7-oxabicyclo[2.2.1]hept-5-ene as a mixture of exo form:endo form=7:3 (1.75 g, 10.4 mmol, yield 52.0%).

IR(neat, $cm^{-1}$): 2986, 1734, 1450, 1369, 1340, 1315, 1277, 1192, 1095, 1047, 1024.

$^1$H-NMR (250 MHz, $CDCl_3$, TMS, ppm) δ: exo form: 6.42–6.32 (2H, m), 5.19 (1H, s), 5.08 (1H, d, J=4.5 Hz), 4.19 (2H, q, J=7.2 Hz), 2.45–2.40 (1H, m), 2.22–2.19 (1H, m), 1.68–1.48 (1H, m), 1.28 (3H, t, J=7.2 Hz) endo form: 6.46–6.43 (1H, m), 6.25–6.22 (1H, m), 5.18–5.16 (1H, m), 5.03–5.01 (1H, m), 4.10 (2H, q, J=7.2 Hz), 3.18–3.05 (1H, m), 2.18–2.02 (1H, M), 1.68–1.52 (1H, m), 1.24 (3H, t, J=7.2 Hz).

EIMS m/z: 139[$(M-C_2H_5)^+$], 123[$(M-C_2H_5O)^+$], 99, 68, 55, 39, 28.

HRMS calcd for $C_9H_{12}O_3(M^+)$: 168.0786, Found m/z= 168.0771.

Reference Example 2

Synthesis of ethyl 5-hydroxy-1,3-cyclohexadiene-1-carboxylate

To a solution (10.72 ml, 1.0 mol/l, 10.72 mmol) of lithium hexamethyldisilazide in tetrahydrofuran was added tetrahydrofuran (60 ml), and the mixture was cooled to −78° C. To this solution was added dropwise a solution of 2-15 ethoxycarbonyl-7-oxabicyclo[2.2.1]hept-5-ene (a mixture of exo form:endo form=7:3, 1.64 g, 9.75 mmol, obtained in Reference Example 1) in tetrahydrofuran (12 ml). After the dropwise addition, the mixture was heated to 0° C. and stirred for 1.5 h. To this reaction mixture was added saturated aqueous ammonium chloride solution (50 ml), and the mixture was extracted with chloroform (100 ml). The organic layer was partitioned, washed with saturated brine (20 ml), and dried over anhydrous sodium sulfate. The components having a low boiling point, such as the solvent and the like, were distilled away. The obtained residue was purified by silica gel column chromatography (eluent: ethyl acetate/hexane=1/5 (volume ratio)) to give ethyl 5-hydroxy-1,3-cyclohexadiene-1-carboxylate (1.52 g, 9.06 mmol, yield 93.9).

IR(neat, $cm^{-1}$): 3412, 3045, 2982, 2937, 2906, 1705, 1641, 1577, 1446, 1402, 1367, 1255, 1203, 1099, 1059, 1026.

$^1$H-NMR (250 MHz, $CDCl_3$, TMS, ppm) δ: 7.12–7.03 (1H, m), 6.31–6.18 (2H, m), 4.45–4.32 (1H, m), 4.23 (2H, q, J=7.2 Hz), 3.00–2.85 (1H, m), 2.71–2.54 (1H, m), 1.58 (1H, s), 1.31 (3H, t, J=7.2 Hz).

Reference Example 3

Synthesis of ethyl (1β,5α,6β)-5-hydroxy-7-oxabicyclo[4.1.0]hept-2-ene-3-carboxylate Ethyl 5-hydroxy-1,3-cyclohexadiene-1-carboxylate (2.84 g, 16.88 mmol), obtained according to the method of Reference Example 2, was dissolved in dichloromethane (20 ml), and sodium hydrogen carbonate (7.09 g, 84.4 mmol) was added. The mixture was cooled to 0° C. and to this solution was added dropwise a solution of 80% m-chloroperbenzoic acid (4.00 g, 18.57 mmol) in dichloromethane (30 ml). After the dropwise addition, the mixture was heated to room temperature and stirred for 12 h. The solid in the reaction mixture was filtered off, and the filtrate was washed with 5% aqueous sodium sulfite solution (30 ml) and saturated brine (20 ml), and dried over anhydrous sodium sulfate. The components having a low boiling point, such as the solvent and the like, were distilled away. The obtained residue was purified by silica gel column chromatography (eluent: ethyl acetate/hexane=1/5 (volume ratio)) to give ethyl (1β,5α,6β)-5-hydroxy-7-oxabicyclo[4.1.0]hept-2-ene-3-carboxylate (2.61 g, 14.17 mmol, yield 83.9%).

IR(neat, cm$^{-1}$): 3435, 2984, 2908, 1712, 1645, 1373, 1251, 1188, 1091, 1057.

$^1$H-NMR (250 MHz, CDCl$_3$, TMS, ppm) δ: 7.03–7.00 (1H, m), 4.21 (2H, q, J=7.2 Hz), 4.22–4.06 (1H, m), 3.69–3.61 (1H, m), 3.56–3.45 (1H, m), 3.01–2.83 (1H, m), 2.00 (1H, s), 1.29 (3H, t, J=7.2 Hz).

EIMS m/z: 166[(M-2H$_2$O)$^+$], 155[(M-C$_2$H$_5$)$^+$], 138[(M-C$_2$H$_5$—H$_2$O)$^+$], 110[(M-CO$_2$C$_2$H$_5$)$^+$], 82, 53.

HRMS: calcd for C$_9$H$_{12}$O$_4$(M$^+$) 184.0735, Found m/z=184.0726.

Example 1

Synthesis of ethyl (3β,4α,5α)-3-benzhydrylamino-4,5-dihydroxy-1-cyclohexene-1-carboxylate Ethyl (1β,5α,6β)-5-hydroxy-7-oxabicyclo[4.1-O]hept-2-ene-3-carboxylate (245 mg, 1.33 mmol) obtained in Reference Example 3 was dissolved in tetrahydrofuran (0.5 ml), and benzhydrylamine (365 mg, 2.00 mmol) was added. The mixture was stirred at 65° C. for 2 days. The reaction mixture was cooled to room temperature, and the components having a low boiling point, such as the solvent and the like, were distilled away. The obtained residue was purified by silica gel column chromatography (eluent: ethyl acetate/hexane=1/1 (volume ratio)) to give ethyl (3β,4α,5α)-3-benzhydrylamino-4,5-dihydroxy-1-cyclohexene-1-carboxylate (457 mg, 1.24 mmol, yield 93.5%).

IR(neat, cm$^{-1}$): 3437, 3061, 3028, 2984, 2906, 1709, 1649, 1452, 1367, 1265, 1076, 1047.

$^1$H-NMR (250 MHz, CDCl$_3$, TMS, ppm) δ: 7.46–7.22 (10H, m), 6.99–6.98 (1H, m), 5.16 (1H, s), 4.20 (2H, q, J=7.2 Hz), 3.53–3.38 (2H, m), 2.55–2.54 (2H, m), 1.29 (3H, t, J=7.2 Hz).

EIMS m/z: 367(M$^+$), 307[(M-C$_2$H$_4$O$_2$)$^+$], 200[(M-CHPh$_2$)$^+$], 167.

HRMS: calcd for C$_{22}$H$_{25}$NO$_4$(M$^+$) 367.1784, Found m/z=367.1785.

Example 2

Synthesis of ethyl (1α,5α,6α)-7-diphenylmethyl-5-methanesulfonyloxy-7-azabicyclo[4.1.0]hept-2-ene-3-carboxylate Ethyl (3β,4α,5α)-3-benzhydrylamino-4,5-dihydroxy-1-cyclohexene-1-carboxylate (110 mg, 0.299 mmol) obtained in Example 1 was dissolved in tetrahydrofuran (2 ml), and triethylamine (1 ml) was added. The mixture was stirred at room temperature for 5 min and cooled to 0° C. To this solution was added dropwise methanesulfonyl chloride (103 mg, 0.687 mmol), and after the dropwise addition, the mixture was heated to 65° C. and stirred for 24 h. The reaction mixture was cooled to room temperature and concentrated. The residue was diluted with dichloromethane (20 ml), washed with saturated aqueous sodium hydrogen carbonate solution (20 ml) and saturated brine (10 ml), and dried over anhydrous sodium sulfate. The components having a low boiling point, such as the solvent and the like, were distilled away. The obtained residue was purified by silica gel column chromatography (eluent: ethyl acetate/hexane=1/3 (volume ratio)) to give ethyl (1α,5α,6α)-7-diphenylmethyl-5-methanesulfonyloxy-7-azabicyclo[4.1.0]hept-2-ene-3-carboxylate (71.3 mg, 0.167 mmol, yield 55.7%).

IR(neat, cm$^{-1}$): 3022, 1705, 1359, 1267, 1217, 1172, 1095.

$^1$H-NMR (250 MHz, CDCl$_3$, TMS, ppm) δ: 7.23–7.19 (11H, m), 5.32–5.28 (1H, m), 4.21 (2H, q, J=7.2 Hz), 3.83 (1H, s), 3.09–2.98 (1H, m), 2.97 (3H, s), 2.68–2.55 (2H, m), 2.41–2.32 (1H, m), 1.31 (3H, t, J=7.2 Hz).

EIMS m/z: 331[(M-O$_3$SCH$_3$)$^+$], 167.

HRMS calcd for C$_{23}$H$_{25}$NO$_5$S(M$^+$): 427.1454, Found m/z=427.1452.

Example 3

Synthesis of ethyl (1α,5α,6α)-7-diphenylmethyl-5-(1-ethylpropoxy)-7-azabicyclo[4.1.0]hept-3-ene-3-carboxylate Ethyl (1α,5α,6α)-7-diphenylmethyl-5-methanesulfonyloxy-7-azabicyclo[4.1.0]hept-2-ene-3-carboxylate (235 mg, 0.55 mmol) obtained according to the method of Example 2, 3-pentanol (6 ml) and dichloromethane (2 ml) were mixed and dissolved. To this solution was added boron trifluoride etherate (390 mg, 2.45 mmol) at room temperature, and the mixture was stirred at room temperature for 3 h. To this reaction mixture was added triethylamine (556 mg, 5.49 mmol) at room temperature, and the mixture was stirred at room temperature for 1 more h. The reaction mixture was concentrated, and the residue was diluted with diethyl ether (20 ml), washed with saturated aqueous sodium hydrogen carbonate solution (10 ml) and saturated brine (5 ml), and dried over anhydrous sodium sulfate. The components having a low boiling point, such as the solvent and the like, were distilled away. The obtained residue was purified by silica gel column chromatography (eluent: ethyl acetate/hexane=1/3 (volume ratio)) to give ethyl (1α,5α,6α)-7-diphenylmethyl-5-(1-ethylpropoxy)-7-azabicyclo[4.1.0]hept-3-ene-3-carboxylate (197 mg, 0.47 mmol, yield 85.6%).

IR(neat, cm$^{-1}$): 2968, 2934, 2876, 1714, 1660, 1493, 1302, 1248, 1080, 1060.

$^1$H-NMR (250 MHz, CDCl$_3$, TMS, ppm) δ: 7.41–7.21 (10H, m), 6.81–6.75 (1H, m), 4.19 (2H, q, J=7.2 Hz), 4.10–4.01 (1H, m), 3.71 (1H, s), 3.17–3.07 (1H, m), 2.76–2.65 (1H, m), 2.64–2.48 (1H, m), 2.18–2.08 (1H, m), 2.00–1.91 (1H, m), 1.49–1.34 (4H, m), 1.31 (3H, t, J=7.2 Hz), 0.86–0.78 (6H, m).

EIMS m/z: 419(M$^+$), 346[(M-CO$_2$C$_2$H$_5$)$^+$], 305, 167.

HRMS: calcd for C$_{27}$H$_{33}$NO$_3$(M$^+$): 419.2461, Found m/z=419.2464.

Example 4

Synthesis of ethyl (1α,5α,6α)-5-(1-ethylpropoxy)-7-azabicyclo[4.1.0]hept-3-ene-3-carboxylate Ethyl (1α,5α,6α)-7-diphenylmethyl-5-(1-ethylpropoxy)-7-azabicyclo[4.1.0]hept-3-ene-3-carboxylate (17 mg, 0.0405 mmol) obtained in Example 3 and 10% palladium-carbon (17 mg) were placed in a flask and the mixture was cooled to 0° C. Thereto was added formic acid (4.4% methanol solution, 1 ml) cooled to 0° C. and the mixture was stirred at 0° C. for 3 h. The reaction mixture was filtrated and the filtrate was concentrated. The residue was diluted with dichloromethane (10 ml), washed with saturated aqueous sodium hydrogen carbonate solution (10 ml) and saturated brine (5 ml), and dried over anhydrous sodium sulfate. The components having a low boiling point, such as the solvent and the like, were distilled away. The obtained residue was purified by silica gel column chromatography (eluent: ethyl acetate/hexane=1/4→5/1 (volume ratio)) to give ethyl (1α, 5α,6α)-5-(1-ethylpropoxy)-7-azabicyclo[4.1.0]hept-3-ene-3-carboxylate (4.3 mg, 0.0169 mmol, yield 41.7%), and the starting material: ethyl (1α,5α,6α)-7-diphenylmethyl-5-(1-ethylpropoxy)-7-azabicyclo[4.1.0]hept-3-ene-3-carboxylate (6.75 mg) was recovered (0.0161 mmol, recovery yield 39.7%).

IR(neat, cm$^{-1}$): 2962, 2926, 2854, 1716, 1462, 1381, 1251, 1130, 1084, 1057.

$^1$H-NMR (500 MHz, CDCl$_3$, TMS, ppm) δ: 6.79–6.78 (1H, m), 4.33–4.32 (1H, m), 4.18 (2H, q, J=7.2 Hz), 3.41–3.38 (1H, m), 2.84–2.80 (1H, m), 2.64–2.60 (1H, m), 2.53–2.51 (1H, m), 2.43–2.42 (1H, m), 1.58–1.53 (1H, m), 1.27 (3H, t, J=7.2 Hz), 0.96 (3H, t, J=7.5 Hz), 0.91 (3H, t, J=7.5 Hz).

EIMS m/z: 253(M$^+$), 224[(M-C$_2$H$_5$)$^+$], 208[(M-OC$_2$H$_5$)$^+$], 182[(M-C$_5$H$_{11}$)$^+$], 166[(M-OC$_5$H$_{11}$)$^+$], 154, 137, 110, 93.

HRMS calcd for C$_{14}$H$_{23}$NO$_3$(M$^+$): 253.1678, Found m/z= 253.1695.

Example 5

Synthesis of ethyl (3β,4α,5α)-3-benzylamino-4,5-dihydroxy-1-cyclohexene-1-carboxylate Ethyl (1β,5α,60)-5-hydroxy-7-oxabicyclo[4.1.0]hept-2-ene-3-carboxylate (1.00 g, 5.42 mmol) obtained in Reference Example 3 was dissolved in tetrahydrofuran (1 ml), and benzylamine (0.652 g, 5.96 mmol) was added. The mixture was stirred at 50° C. for 18 h and the reaction mixture was cooled to room temperature. The components having a low boiling point, such as the solvent and the like, were distilled away. The obtained residue was purified by silica gel column chromatography (eluent: ethyl acetate/hexane=5/1 (volume ratio)) to give ethyl (3β,4α,5α)-3-benzylamino-4,5-dihydroxy-1-cyclohexene-1-carboxylate (1.49 g, 5.10 mmol, yield 94.1%).

IR(neat, cm$^{-1}$): 3402, 2982, 2905, 1709, 1651, 1454, 1367, 1255, 1080.

$^1$H-NMR (250 MHz, CDCl$_3$, TMS, ppm) δ: 7.39–7.26 (5H, m), 6.96 (1H, s), 4.29–4.21 (1H, m), 4.21 (2H, q, J=7.2 Hz), 3.93 (2H, dd, J=53, 13 Hz), 3.48 (1H, s), 3.52–3.40 (1H, m), 2.82–2.45 (2H, m), 1.29 (3H, t, J=7.2 Hz).

EIMS m/z: 291(M$^+$), 255[(M-2H$_2$O)$^+$], 231, 91.

HRMS calcd for C$_{16}$H$_{21}$NO$_4$(M$^+$): 291.1471, Found m/z= 291.1457.

Example 6

Synthesis of ethyl (3β,4α,5α)-3-{N-(tert-butoxycarbonyl)-N-benzylamino}-4,5-dihydroxy-1-cyclohexene-1-carboxylate Ethyl (3β,4α,5α)-3-benzylamino-4,5-dihydroxy-1-cyclohexene-1-carboxylate (1.48 g, 5.07 mmol) obtained in Example 5 was dissolved in acetonitrile (10 ml), and di-tert-butyl dicarbonate (1.22 g, 5.58 mmol) was added. The mixture was stirred at room temperature for 1.5 h and, after the completion of the reaction, the components having a low boiling point, such as the solvent and the like, were distilled away. The obtained residue was purified by silica gel column chromatography (eluent: ethyl acetate/hexane=1/3 (volume ratio)) to give ethyl (3β,4α,5α)-3-{N-(tert-butoxycarbonyl)-N-benzylamino}-4,5-dihydroxy-1-cyclohexene-1-carboxylate (1.75 g, 4.47 mmol, yield 88.2%).

IR(neat, cm$^{-1}$): 3441, 3011, 2980, 2934, 1693, 1454, 1410, 1367, 1253, 1165, 1084.

EIMS m/z: 391(M$^+$), 335[(M-C$_4$H$_8$)$^+$], 290[(M-C$_4$H$_9$CO$_2$)$^+$], 231, 91.

HRMS calcd for C$_{21}$H$_{29}$NO$_6$(M$^+$): 391.1995, Found m/z= 391.1987.

Example 7

Synthesis of ethyl (3β,4α,5α)-3-{N-(tert-butoxycarbonyl)-N-benzylamino}-4,5-dimethanesulfonyloxy-1-cyclohexene-1-carboxylate Ethyl (3β,4α,5α)-3-{N-(tert-butoxycarbonyl)-N-benzylamino}-4,5-dihydroxy-1-cyclohexene-1-carboxylate (1.73 g, 4.42 mmol) obtained in Example 6 was dissolved in methylene chloride (20 ml), and triethylamine (1.12 g, 11.05 mmol) was added. The mixture was stirred at room temperature for 5 min and this reaction mixture was cooled to 0° C. Methanesulfonyl chloride (1.11 g, 9.72 mmol) was added dropwise over 5 min and, after the dropwise addition, the mixture was stirred at room temperature for 1.5 h. The components having a low boiling point, such as the solvent and the like, were distilled away. The obtained residue was purified by silica gel column chromatography (eluent: ethyl acetate/hexane=1/5 (volume ratio)) to give ethyl (3β,4α, 5α)-3-{N-(tert-butoxycarbonyl)-N-benzylamino}-4,5-dimethanesulfonyloxy-1-cyclohexene-1-carboxylate (2.41 g, 4.40 mmol, yield 99.6%).

IR(neat, cm$^{-1}$): 2980, 2939, 1701, 1454, 1419, 1359, 1246, 1176, 1091, 1057, 1005.

EIMS m/z: 491[(M-C$_4$H$_8$)$^+$], 381, 244, 150, 106, 91.

HRMS calcd for C$_{19}$H$_{25}$NO$_{10}$S$_2$[(M-C$_4$H$_8$)$^+$]: 491.0920, Found m/z=491.0901.

Example 8

Synthesis of ethyl (3β,4α,5α)-3-benzylamino-4,5-dimethanesulfonyloxy-1-cyclohexene-1-carboxylate Ethyl (3β,4α,5α)-3-{N-(tert-butoxycarbonyl)-N-benzylamino}-4,5-dimethanesulfonyloxy-1-cyclohexene-1-carboxylate (2.11 g, 3.85 mmol) obtained according to the method of Example 7 was dissolved in methylene chloride (66 ml), 20 and trifluoroacetic acid (4.4 g, 38.5 mmol) was added. The mixture was stirred at room temperature for 18 h. The reaction mixture was washed with saturated aqueous sodium hydrogen carbonate solution (50 ml) and saturated brine (20 ml), and dried over anhydrous sodium sulfate. The components having a low boiling point, such as the solvent and the like, were distilled away. The obtained residue was purified by silica gel column chromatography (eluent: ethyl acetate/hexane=1/5 (volume ratio)) to give ethyl (3β,4α, 5α)-3-benzylamino-4,5-dimethanesulfonyloxy-1-cyclohexene-1-carboxylate (1.65 g, 3.69 mmol, yield 96.0%).

IR(neat, cm$^{-1}$): 3028, 2984, 2939, 2361, 1712, 1653, 1454, 1359, 1249, 1176, 1095, 1045, 1003.

$^1$H-NMR (250 MHz, CDCl$_3$, TMS, ppm) δ: 7.38–7.25 (5H, m), 6.87–6.79 (1H, m), 5.28–5.18 (1H, m), 4.89–4.79 (1H, m), 4.22 (2H, q, J=7.2 Hz), 3.92 (2H, dd, J=22.5, 14.2 Hz), 3.81–3.70 (1H, m), 3.12 (1H, s), 3.19 (1H, s), 2.88–2.78 (2H, m), 1.30 (3H, t, J=7.2 Hz).

Example 9

Synthesis of ethyl (1α,5α,6α)-7-benzyl-5-methanesulfonyloxy-7-azabicyclo[4.1.0]hept-2-ene-3-carboxylate Ethyl (3β,4α,5α)-3-benzylamino-4,5-dimethanesulfonyloxy-1-cyclohexene-1-carboxylate (0.278 g, 0.62 mmol) obtained in Example 8 was dissolved in tetrahydrofuran (1 ml), and triethylamine (1 ml) was added. The mixture was stirred at 50° C. for 2 days. The reaction mixture was cooled to room temperature. The components having a low boiling point, such as the solvent and the like, were distilled away. The obtained residue was purified by silica gel column chromatography (eluent: ethyl acetate/hexane=1/3 (volume ratio)) to give ethyl (3α,5α,5α)-7-benzyl-5-methanesulfonyloxy-7-azabicyclo[4.1.0]hept-2-ene-3-carboxylate (0.124 g, 0.352 mmol, yield 56.7%).

IR(neat, cm$^{-1}$): 1707, 1358, 1265, 1209, 1172, 1095.

$^1$H-NMR (250 MHz, CDCl$_3$, TMS, ppm) δ: 7.39–7.20 (6H, m), 5.47–5.37 (1H, m), 4.19 (2H, q, J=7.2 Hz), 3.59 (2H, dd, J=75, 14 Hz), 3.00 (1H, s), 3.05–2.89 (1H, m), 2.65–2.38 (2H, m), 2.34–2.22 (1H, m), 1.28 (3H, t, J=7.2 Hz).

EIMS m/z: 351(M$^+$), 256[(M-O$_3$SCH$_3$)$^+$], 164, 91.

HRMS calcd for C$_{17}$H$_{21}$NO5S(M$^+$): 351.1141, Found m/z=351.1110.

Example 10

Synthesis of ethyl (1α,5α,6α)-7-benzyl-5-(1-ethylpropoxy)-7-azabicyclo[4.1.0]hept-3-ene-3-carboxylate Ethyl (1α,5α,6α)-7-benzyl-5-methanesulfonyloxy-7-azabicyclo[4.1.0]hept-2-ene-3-carboxylate (50 mg, 0.142 mol) obtained in Example 9 was dissolved in 3-pentanol (1 ml), and boron trifluoride etherate (22.2 mg, 0.156 mmol) was added at room temperature. The mixture was stirred at 65° C. for 3 h. The reaction mixture was cooled to room temperature. Triethylamine (21.6 mg, 0.213 mmol) was added and the mixture was stirred at room temperature for 1 h. The reaction mixture was concentrated, and the residue was diluted with diethyl ether (10 ml), washed with saturated aqueous sodium hydrogen carbonate solution (5 ml) and saturated brine (3 ml), and dried over anhydrous sodium sulfate. The components having a low boiling point, such as the solvent and the like, were distilled away. The obtained residue was purified by silica gel column chromatography (eluent: ethyl acetate/hexane=1/3 (volume ratio)) to give ethyl (1α,5α,6α)-7-benzyl-5-(1-ethylpropoxy)-7-azabicyclo[4.1.0]hept-3-ene-3-carboxylate (42.8 mg, 0.125 mmol, yield 87.7%).

IR(neat, cm$^{-1}$): 2968, 2934, 2876, 1714, 1454, 1369, 1302, 1248, 1080, 1059.

$^1$H-NMR (250 MHz, CDCl$_3$, TMS, ppm) δ: 7.33–7.28 (5H, m), 6.78–6.77 (1H, m), 4.30–4.20 (1H, m), 4.16 (2H, q, J=7.2 Hz), 3.58 (1H, s), 3.40–3.21 (1H, m), 2.83–2.66 (1H, m), 2.65–2.48 (1H, m), 2.11–2.00 (1H, m), 2.00–1.88 (1H, m), 1.68–1.43 (4H, m), 1.25 (3H, t, J=7.2 Hz), 0.93 (3H, t, J=7.4 Hz), 0.89 (3H, t, J=7.4 Hz).

EIMS m/z: 343(M$^+$), 314[(M-C$_2$H$_5$)$^+$], 272[(M-C$_5$H$_{11}$)$^+$], 256, 200, 91

HRMS calcd for C$_{21}$H$_{29}$NO$_3$(M$^+$): 343.2148, Found m/z=343.2147.

Example 11

Synthesis of ethyl (1α,5α,6α)-5-(1-ethylpropoxy)-7-azabicyclo[4.1.0]hept-3-ene-3-carboxylate Ethyl (1α,5α,6α)-7-benzyl-5-(1-ethylpropoxy)-7-azabicyclo[4.1.0]hept-3-ene-3-carboxylate (19 mg, 0.055 mmol) obtained in Example 10 and 10% palladium-carbon (19 mg) were placed in a flask and formic acid (4.4% methanol solution, 1 ml) was added at room temperature. The mixture was stirred at room temperature for 10 min. The reaction mixture was filtrated and the filtrate was concentrated. The residue was diluted with dichloromethane (10 ml), washed with saturated aqueous sodium hydrogen carbonate solution (10 ml) and saturated brine (5 ml), and dried over anhydrous sodium sulfate. The components having a low boiling point, such as the solvent and the like, were distilled away. The obtained residue was purified by silica gel column chromatography (eluent:ethyl acetate/hexane=1/4→5/1 (volume ratio)) to give ethyl (1α,5α,6α)-5-(1-ethylpropoxy)-7-azabicyclo[4.1.0]hept-3-ene-3-carboxylate (8.1 mg, 0.0319 mmol, yield 58.0%).

IR(neat, cm$^{-1}$): 2962, 2926, 2854, 1716, 1462, 1381, 1251, 1130, 1084, 1057.

$^1$H-NMR (500 MHz, CDCl$_3$, TMS, ppm) δ: 6.79–6.78 (1H, m), 4.33–4.32 (1H, m), 4.18 (2H, q, J=7.2 Hz), 3.41–3.38 (1H, m), 2.84–2.80 (1H, m), 2.64–2.60 (1H, m), 2.53–2.51 (1H, m), 2.43–2.42 (1H, m), 1.58–1.53 (1H, m), 1.27 (3H, t, J=7.2 Hz), 0.96 (3H, t, J=7.5 Hz), 0.91 (3H, t, J=7.5 Hz).

EIMS m/z: 253(M$^+$), 224[(M-C$_2$H$_5$)$^+$], 208[(M-OC$_2$H$_5$)$^+$], 182[(M-C$_5$H$_{11}$)$^+$], 166[(M-OC$_5$H$_{11}$)$^+$], 154, 137, 110, 93.

HRMS calcd for C$_{14}$H$_{23}$NO$_3$(M$^+$): 253.1678, Found m/z=253.1695.

The α and β show the relative configuration of the substituents on the ring. The relative configuration of Example compounds are shown in the following, where α is conveniently placed on the upper side of the sheet and β on the lower side of the sheet, but these structural formulas do not represent the absolute configuration. Dpm means diphenylmethyl, Bzl means benzyl, Boc means tert-butoxycarbonyl, Ms means methanesulfonyl and Et means ethyl.

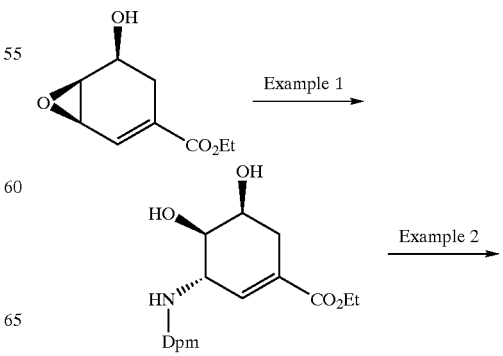

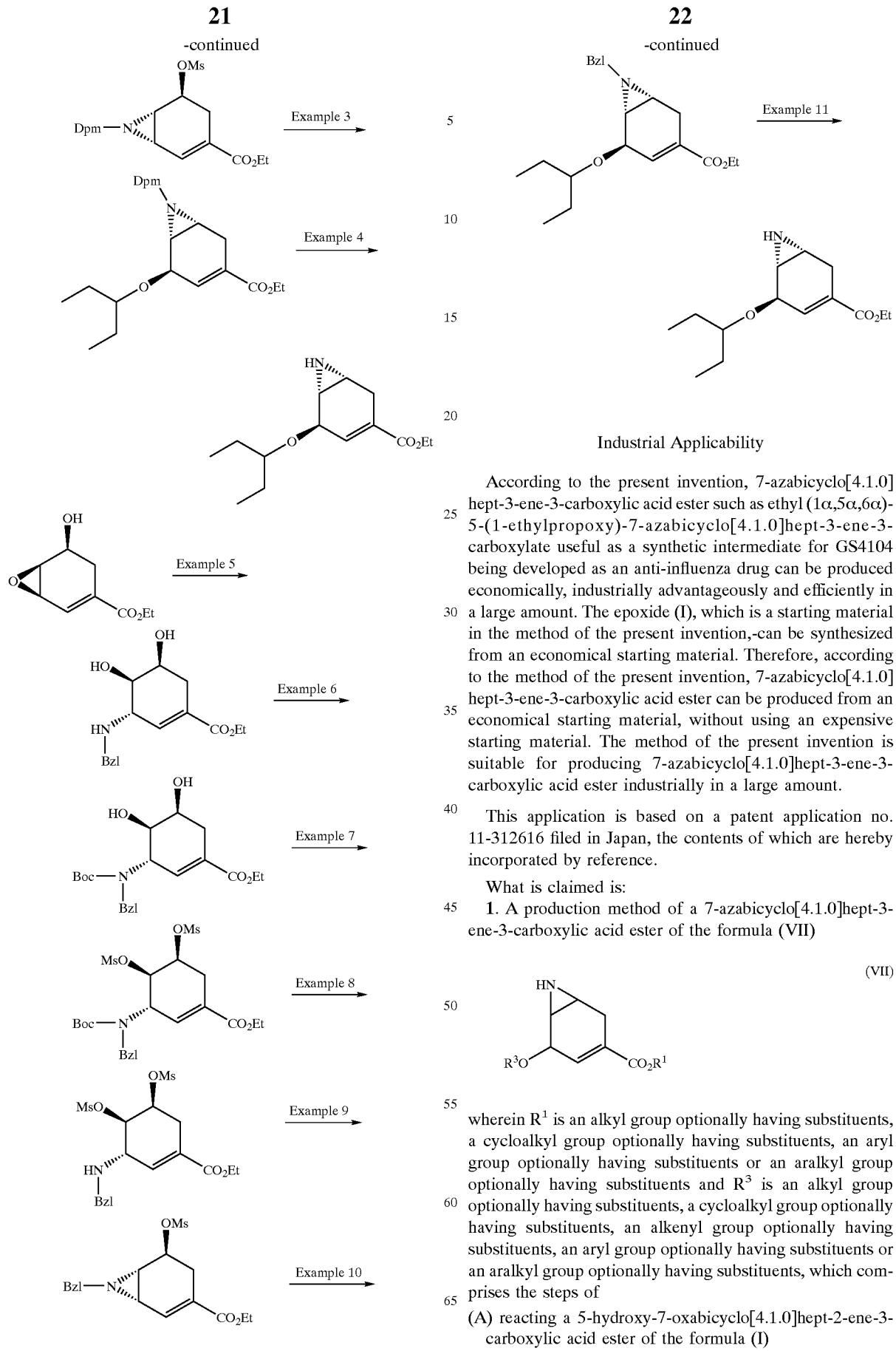

Industrial Applicability

According to the present invention, 7-azabicyclo[4.1.0]hept-3-ene-3-carboxylic acid ester such as ethyl (1α,5α,6α)-5-(1-ethylpropoxy)-7-azabicyclo[4.1.0]hept-3-ene-3-carboxylate useful as a synthetic intermediate for GS4104 being developed as an anti-influenza drug can be produced economically, industrially advantageously and efficiently in a large amount. The epoxide (I), which is a starting material in the method of the present invention,-can be synthesized from an economical starting material. Therefore, according to the method of the present invention, 7-azabicyclo[4.1.0]hept-3-ene-3-carboxylic acid ester can be produced from an economical starting material, without using an expensive starting material. The method of the present invention is suitable for producing 7-azabicyclo[4.1.0]hept-3-ene-3-carboxylic acid ester industrially in a large amount.

This application is based on a patent application no. 11-312616 filed in Japan, the contents of which are hereby incorporated by reference.

What is claimed is:

1. A production method of a 7-azabicyclo[4.1.0]hept-3-ene-3-carboxylic acid ester of the formula (VII)

(VII)

wherein $R^1$ is an alkyl group optionally having substituents, a cycloalkyl group optionally having substituents, an aryl group optionally having substituents or an aralkyl group optionally having substituents and $R^3$ is an alkyl group optionally having substituents, a cycloalkyl group optionally having substituents, an alkenyl group optionally having substituents, an aryl group optionally having substituents or an aralkyl group optionally having substituents, which comprises the steps of (A) reacting a 5-hydroxy-7-oxabicyclo[4.1.0]hept-2-ene-3-carboxylic acid ester of the formula (I)

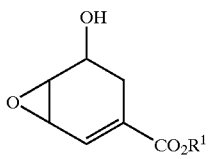

(I)

wherein R¹ is as defined above, with an amine of the formula (II)

R²NH₂ (II)

wherein R² is a hydrogen atom, an alkyl group optionally having substituents, a cycloalkyl group optionally having substituents, an alkenyl group optionally having substituents, an aryl group optionally having substituents or an aralkyl group optionally having substituents, to give a 3-amino-4,5-dihydroxy-1-cyclohexene-1-carboxylic acid ester of the formula (III)

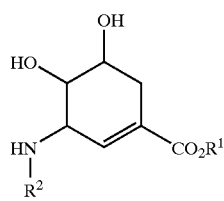

(III)

wherein R¹ and R² are as defined above, (B) reacting the obtained 3-amino-4,5-dihydroxy-1-cyclohexene-1-carboxylic acid ester with a sulfonylating agent in the presence of a base to give a 5-sulfonyloxy-7-azabicyclo[4.1.0]hept-2-ene-3-carboxylic acid ester of the formula (IV)

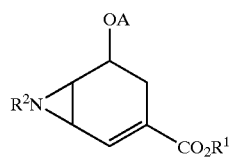

(IV)

wherein R¹ and R² are as defined above and A is an organic sulfonyl group, (C) reacting the obtained 5-sulfonyloxy-7-azabicyclo[4.1.0]hept-2-ene-3-carboxylic acid ester with an alcohol of the formula (V)

R³OH (V)

wherein R³ is as defined above, in the presence of a Lewis acid to give a 5-oxy-7-azabicyclo[4.1.0]hept-3-ene-3-carboxylic acid ester of the formula (VI)

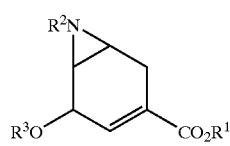

(VI)

wherein R¹, R² and R³ are as defined above, and (D) when R² is an alkyl group optionally having substituents, a cycloalkyl group optionally having substituents, an alkenyl group optionally having substituents, an aryl group optionally having substituents or an aralkyl group optionally having substituents, eliminating the 7-position substituent R² of the obtained 5-oxy-7-azabicyclo[4.1.0]hept-3-ene-3-carboxylic acid ester.

2. A production method of a 7-azabicyclo[4.1.0]hept-3-ene-3-carboxylic acid ester of the formula (VII)

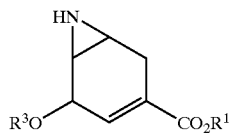

(VII)

wherein R¹ is an alkyl group optionally having substituents, a cycloalkyl group optionally having substituents, an aryl group optionally having substituents or an aralkyl group optionally having substituents and R³ is an alkyl group optionally having substituents, a cycloalkyl group optionally having substituents, an alkenyl group optionally having substituents, an aryl group optionally having substituents or an aralkyl group optionally having substituents, which comprises the steps of (A) reacting a 5-hydroxy-7-oxabicyclo[4.1.0]hept-2-ene-3-carboxylic acid ester of the formula (I)

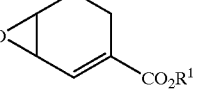

(I)

wherein R¹ is as defined above, with an amine of the formula (II)

R²NH₂ (II)

wherein R² is a hydrogen atom, an alkyl group optionally having substituents, a cycloalkyl group optionally having substituents, an alkenyl group optionally having substituents, an aryl group optionally having substituents or an aralkyl group optionally having substituents, to give a 3-amino-4,5-dihydroxy-1-cyclohexene-1-carboxylic acid ester of the formula (III)

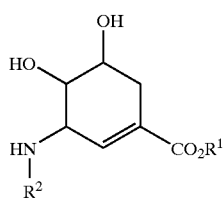

(III)

wherein R¹ and R² are as defined above, (B) protecting an amino group of the obtained 3-amino-4,5-dihydroxy-1-cyclohexene-1-carboxylic acid ester to give a 3-amino-4,5-dihydroxy-1-cyclohexene-1-carboxylic acid ester of the formula (VIII)

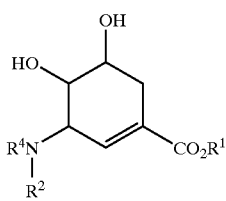

(VIII)

wherein R¹ and R² are as defined above and R⁴ is an amino-protecting group, (C) reacting the obtained 3-amino-4,5-dihydroxy-1-cyclohexene-1-carboxylic acid ester with a sulfonylating agent in the presence of a base to give a 3-amino-4,5-disulfonyloxy-1-cyclohexene-1-carboxylic acid ester of the formula (IX)

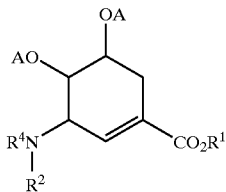

(IX)

wherein R¹, R² and R⁴ are as defined above and A is an organic sulfonyl group, (D) removing the amino-protecting group from the obtained 3-amino-4,5-disulfonyloxy-1-cyclohexene-1-carboxylic acid ester to give a 3-amino-4,5-disulfonyloxy-1-cyclohexene-1-carboxylic acid ester of the formula (X)

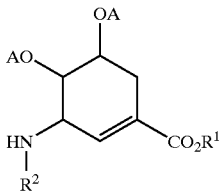

(X)

wherein R¹, R² and A are as defined above, (E) reacting the obtained 3-amino-4,5-disulfonyloxy-1-cyclohexene-1-carboxylic acid ester with a base to give a 5-sulfonyloxy-7-azabicyclo[4.1.0]hept-2-ene-3-carboxylic acid ester of the formula (IV)

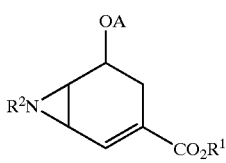

(IV)

wherein R¹, R² and A are as defined above, (F) reacting the obtained 5-sulfonyloxy-7-azabicyclo[4.1.0]hept-2-ene-3-carboxylic acid ester with an alcohol of the formula (V)

R³OH (V)

wherein R³ is as defined above, in the presence of a Lewis acid to give a 5-oxy-7-azabicyclo[4.1.0]hept-3-ene-3-carboxylic acid ester of the formula (VI)

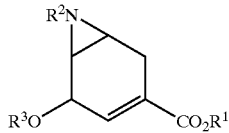

(VI)

wherein R¹, R² and R³ are as defined above, and (G) when R² is an alkyl group optionally having substituents, a cycloalkyl group optionally having substituents, an alkenyl group optionally having substituents, an aryl group optionally having substituents or an aralkyl group optionally having substituents, eliminating the 7-position substituent R² from the obtained 5-oxy-7-azabicyclo[4.1.0]hept-3-ene-3-carboxylic acid ester.

3. A production method of a 7-azabicyclo[4.1.0]hept-3-ene-3-carboxylic acid ester the formula (VII)

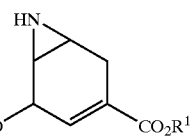

(VII)

wherein R¹ is an alkyl group optionally having substituents, a cycloalkyl group optionally having substituents, an aryl group optionally having substituents or an aralkyl group optionally having substituents and R³ is an alkyl group optionally having substituents, a cycloalkyl group optionally having substituents, an alkenyl group optionally having substituents, an aryl group optionally having substituents or an aralkyl group optionally having substituents, which comprises eliminating a 7-position substituent R²', from a 5-oxy-7-azabicyclo[4.1.0]hept-3-carboxylic acid ester of the formula (VI')

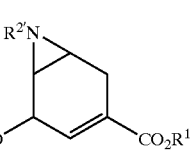

(VI')

wherein R²', is an alkyl group optionally having substituents, a cycloalkyl group optionally having substituents, an alkenyl group optionally having substituents, an aryl group optionally having substituents, an alkenyl group optionally having substituents, and R¹ and R³ are as defined above.

4. A production method of a 5-oxy-7-azabicyclo[4.1.0]hept-3-ene-3-carboxylic acid ester of the formula (VI)

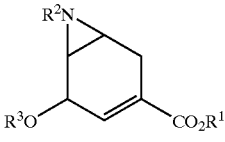

(VI)

wherein R¹ is an alkyl group optionally having substituents, a cycloalkyl group optionally having substituents, an aryl group optionally having substituents or an aralkyl group optionally having substituents, R² is a hydrogen atom, an alkyl group optionally having substituents, a cycloalkyl group optionally having substituents, an alkenyl group optionally having substituents, an aryl group optionally having substituents or an aralkyl group optionally having substituents and $R^3$ is an alkyl group optionally having substituents, a cycloalkyl group optionally having substituents, an alkenyl group optionally having substituents, an aryl group optionally having substituents or an aralkyl group optionally having substituents, which comprises reacting a 5-sulfonyloxy-7-azabicyclo[4.1.0]hept-2-ene-3-carboxylic acid ester of the formula (IV)

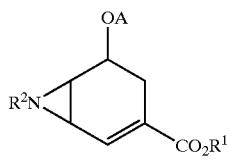

(IV)

wherein A is an organic sulfonyl group, and $R^1$ and $R^2$ are as defined above, with an alcohol of the formula (V)

 $R^3OH$ (V)

wherein $R^3$ is as defined above, in the presence of a Lewis acid.

5. A production method of a 5-sulfonyloxy-7-azabicyclo [4.1.0]hept-2-ene-3-carboxylic acid ester of the formula (IV)

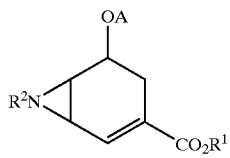

(IV)

wherein $R^1$ is an alkyl group optionally having substituents, a cycloalkyl group optionally having substituents, an aryl group optionally having substituents or an aralkyl group optionally having substituents and $R^2$ is a hydrogen atom, an alkyl group optionally having substituents, a cycloalkyl group optionally having substituents, an alkenyl group optionally having substituents, an aryl group optionally having substituents or an aralkyl group optionally having substituents and A is an organic sulfonyl group, which comprises reacting a 3-amino-4,5-dihydroxy-1-cyclohexene-1-carboxylic acid ester of the formula (III)

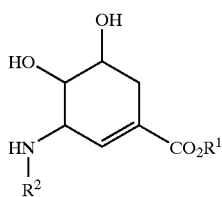

(III)

wherein $R^1$ and $R^2$ are as defined above, with a sulfonylating agent in the presence of a base.

6. A production method of a 5-sulfonyloxy-7-azabicyclo-[4.1.0]hept-2-ene-3-carboxylic acid ester of the formula (IV)

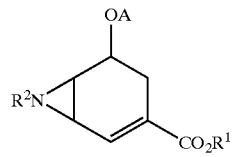

(IV)

wherein $R^1$ is an alkyl group optionally having substituents, a cycloalkyl group optionally having substituents, an aryl group optionally having substituents or an aralkyl group optionally having substituents, $R^2$ is a hydrogen atom, an alkyl group optionally having substituents, a cycloalkyl group optionally having substituents, an alkenyl group optionally having substituents, an aryl group optionally having substituents or an aralkyl group optionally having substituents and A is an organic sulfonyl group, which comprises reacting a 3-amino-4,5-disulfonyloxy-1-cyclohexene-1-carboxylic acid ester of the formula (X)

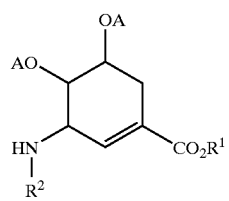

(X)

wherein $R^1$, $R^2$ and A are as defined above, with a base.

7. A production method of a 5-sulfonyloxy-7-azabicyclo [4.1.0]hept-2-ene-3-carboxylic acid ester of the formula (IV)

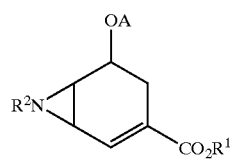

(IV)

wherein $R^1$ is an alkyl group optionally having substituents, a cycloalkyl group optionally having substituents, an aryl group optionally having substituents or an aralkyl group optionally having substituents, $R^2$ is a hydrogen atom, an alkyl group optionally having substituents, a cycloalkyl group optionally having substituents, an alkenyl group optionally having substituents, an aryl group optionally having substituents or an aralkyl group optionally having substituents, and A is an organic sulfonyl group, which comprises (A) protecting an amino group of a 3-amino-4,5-dihydroxy-1-cyclohexene-1-carboxylic acid ester of the formula (III)

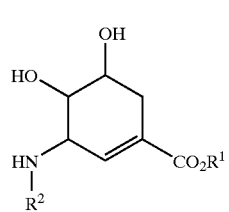

(III)

wherein $R^1$ and $R^2$ are as defined above, to give a 3-amino-4,5-dihydroxy-1-cyclohexene-1-carboxylic acid ester of the formula (VIII)

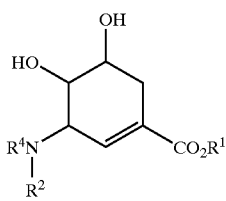

(VIII)

wherein $R^1$ and $R^2$ are as defined above, and $R^4$ is an amino-protecting group, (B) reacting the obtained 3-amino-4,5-dihydroxy-1-cyclohexene-1-carboxylic acid ester with a sulfonylating agent in the presence of a base to give a 3-amino-4,5-disulfonyloxy-1-cyclohexene-1-carboxylic acid ester of the formula

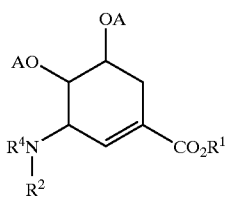

(IX)

wherein $R^1$, $R^2$, $R^4$ and A are as defined above, (C) removing the amino-protecting group of the obtained 3-amino-4,5-disulfonyloxy-1-cyclohexene-1-carboxylic acid ester to give a 3-amino-4,5-disulfonyloxy-1-cyclohexene-1-carboxylic acid ester of the formula (X)

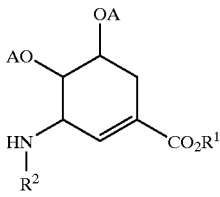

(X)

wherein $R^1$ $R^2$ and A are as defined above, and (D) reacting the obtained 3-amino-4,5-disulfonyloxy-1-cyclohexene-1-carboxylic acid ester with a base.

8. A production method of a 3-amino-4,5-dihydroxy-1-cyclohexene-1-carboxylic acid ester of the formula (III)

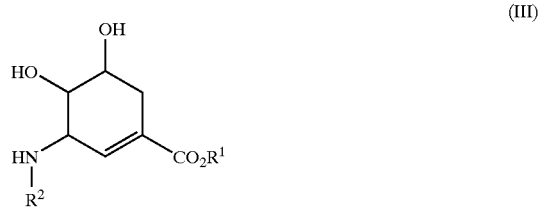

(III)

wherein $R^1$ is an alkyl group optionally having substituents, a cycloalkyl group optionally having substituents, an aryl group optionally having substituents or an aralkyl group optionally having substituents and $R^2$ is a hydrogen atom, an alkyl group optionally having substituents, a cycloalkyl group optionally having substituents, an alkenyl group optionally having substituents, an aryl group optionally having substituents or an aralkyl group optionally having substituents, which comprises reacting a 5-hydroxy-7-oxabicyclo[4.1.0]hept-2-ene-3-carboxylic acid ester of the formula (I)

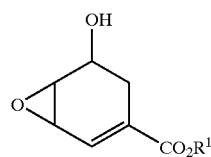

(I)

wherein $R^1$ is as defined above, with an amine of the formula (II)

$R^2NH_2$ (II)

wherein $R^2$ is as defined above.

* * * * *